(12) United States Patent
Todd et al.

(10) Patent No.: US 11,380,424 B2
(45) Date of Patent: Jul. 5, 2022

(54) SYSTEM AND METHOD FOR GENETIC BASED EFFICACY TESTING

(71) Applicant: Xact Laboratories, LLC, Twinsburg, OH (US)

(72) Inventors: Rob Todd, Doylestown, PA (US); Jerry Wrobel, Aurora, OH (US); John Pigott, Slyvania, OH (US)

(73) Assignee: Xact Laboratories LLC, Twinsburg, OH (US)

(*) Notice: Subject to any disclaimer, the term of this patent is extended or adjusted under 35 U.S.C. 154(b) by 370 days.

(21) Appl. No.: 16/674,189

(22) Filed: Nov. 5, 2019

(65) Prior Publication Data

US 2020/0075138 A1    Mar. 5, 2020

Related U.S. Application Data

(63) Continuation-in-part of application No. 16/441,597, filed on Jun. 14, 2019.

(60) Provisional application No. 62/773,424, filed on Nov. 30, 2018, provisional application No. 62/685,479, filed on Jun. 15, 2018.

(51) Int. Cl.
| | |
|---|---|
| *G16H 10/40* | (2018.01) |
| *G16H 15/00* | (2018.01) |
| *G16H 10/60* | (2018.01) |
| *G16H 20/10* | (2018.01) |
| *G16H 70/40* | (2018.01) |
| *G16H 80/00* | (2018.01) |
| *G16H 50/70* | (2018.01) |

(52) U.S. Cl.
CPC .......... *G16H 10/40* (2018.01); *G16H 10/60* (2018.01); *G16H 15/00* (2018.01); *G16H 20/10* (2018.01); *G16H 50/70* (2018.01); *G16H 70/40* (2018.01); *G16H 80/00* (2018.01)

(58) Field of Classification Search
None
See application file for complete search history.

(56) References Cited

U.S. PATENT DOCUMENTS

| 6,315,720 B1 | 11/2001 | Williams et al. |
| 8,386,274 B1 | 2/2013 | Pinsonneault |
| (Continued) | | |

OTHER PUBLICATIONS

PJ Caraballo et al., Electronic Medical Record-Integrated Pharmacogenomics and Related Clinical Decision Support Concepts, Aug. 2017, Clinical Pharmacology & Therapeutics, vol. 102 No 2, pp. 254-264 (Year: 2017).*

(Continued)

*Primary Examiner* — Christopher L Gilligan
*Assistant Examiner* — Karen A Hranek
(74) *Attorney, Agent, or Firm* — Standley Law Group LLP; Adam J. Smith; Jeffrey S. Standley

(57) ABSTRACT

System and methods for alerting a healthcare provider to prescribed treatments having reduced or no effectiveness due to genetic composition is provided. A database containing treatments known to have reduced or no efficacy in persons having particular genetic markers is queried to determine whether any treatments prescribed by, or likely to be prescribed by, a healthcare provider to the patient are known to have reduced or no efficacy in persons having the same genetic markers as the patient. An alert containing such information is displayed at a healthcare provider system.

4 Claims, 11 Drawing Sheets

(56) References Cited

U.S. PATENT DOCUMENTS

| | | | |
|---|---|---|---|
| 10,950,354 B1* | 3/2021 | Belgoroski | G16H 40/20 |
| 2002/0012921 A1 | 1/2002 | Stanton, Jr. | |
| 2002/0115073 A1 | 8/2002 | Papadopoulos et al. | |
| 2002/0147616 A1 | 10/2002 | Pollard et al. | |
| 2003/0040002 A1 | 2/2003 | Ledley | |
| 2005/0107672 A1 | 5/2005 | Lipscher et al. | |
| 2005/0149361 A1* | 7/2005 | Saus | G16H 70/40 705/3 |
| 2006/0259325 A1 | 11/2006 | Patterson | |
| 2007/0178501 A1 | 8/2007 | Rabinowitz et al. | |
| 2008/0091464 A1 | 4/2008 | Lipscher et al. | |
| 2008/0131887 A1 | 6/2008 | Stephan et al. | |
| 2008/0162352 A1 | 7/2008 | Gizewski | |
| 2008/0228824 A1 | 9/2008 | Kenedy et al. | |
| 2009/0094059 A1* | 4/2009 | Coleman | G16H 20/10 705/3 |
| 2009/0198519 A1 | 8/2009 | McNamar | |
| 2010/0070455 A1 | 3/2010 | Halperin et al. | |
| 2010/0317006 A1 | 12/2010 | Soykan et al. | |
| 2012/0065999 A1 | 3/2012 | Takatoku et al. | |
| 2012/0185270 A1 | 7/2012 | Scantland et al. | |
| 2013/0096943 A1 | 4/2013 | Carey et al. | |
| 2013/0246079 A1 | 9/2013 | Hoffman et al. | |
| 2014/0303992 A1 | 10/2014 | Scantland et al. | |
| 2014/0316821 A1* | 10/2014 | Sheffield | G16B 50/00 705/3 |
| 2014/0350954 A1* | 11/2014 | Ellis | G16H 10/60 705/2 |
| 2014/0372141 A1 | 12/2014 | Renner et al. | |
| 2015/0058030 A1 | 2/2015 | Scantland et al. | |
| 2015/0058039 A1* | 2/2015 | Shiloh | G16H 70/40 705/3 |
| 2015/0170291 A1 | 6/2015 | Renner et al. | |
| 2015/0228030 A1 | 8/2015 | Scantland et al. | |
| 2016/0048652 A1* | 2/2016 | Spivey | G16H 70/40 705/2 |
| 2016/0092652 A1 | 3/2016 | Stewart et al. | |
| 2016/0180063 A1 | 6/2016 | Scantland et al. | |
| 2016/0239636 A1* | 8/2016 | O'Donnell | G16B 20/20 |
| 2017/0004282 A1 | 1/2017 | Scantland et al. | |
| 2017/0046491 A1 | 2/2017 | Scantland et al. | |
| 2017/0046492 A1 | 2/2017 | Renner et al. | |
| 2017/0213011 A1 | 7/2017 | Hoffman et al. | |
| 2017/0270246 A1* | 9/2017 | Baskys | G16B 20/00 |
| 2017/0308669 A1* | 10/2017 | Apte | G16H 70/40 |
| 2018/0075220 A1 | 3/2018 | Hill, Sr. et al. | |
| 2018/0308569 A1* | 10/2018 | Luellen | G16H 40/20 |
| 2018/0330060 A1* | 11/2018 | Biles | G16H 50/30 |
| 2019/0244688 A1* | 8/2019 | Wilson | G16H 10/40 |

OTHER PUBLICATIONS

Clinisync, Clinisync Products and Services webpage, http://www.clinisync.org/, Jul. 18, 2018, 5 pages.

Althoff, Lisa, DNA Chip—Genetic Testing of the Future webpage, https://www.ndsu.edu/pubweb/~mcclean/plsc431/students99/althoff.html, Copyright 1999, Aug. 2, 2019, 5 pages.

LabX, DNA Sequencers Listings webpage, https://www.labx.com/dna-sequencers, Aug. 2, 2019, 3 pages.

Vecna, Veena Patient Solutions webpage, https://healthcare.vecna.com/, Jul. 18, 2019, 11 pages.

Translational Software, Making Sense of Pharmacogenomics Testing webpage, https://translationalsoftware.com/, Sep. 11, 2019, 14 pages.

Translational Software, Integrated Into Clinical Systems archived webpage, https://web.archive.org/web/20171217010330/https://translationalsoftware.com/, Oct. 17, 2017, 7 pages.

Translational Software, Insights Ready for Action archived webpage, https://web.archive.org/web/20180829020620/https://translationalsoftwarre.com/, Aug. 29, 2018, 9 pages.

Coriell Life Sciences, GeneDose—Medication Risk Management Tool archived webpage, https://web.archive.org/web/20170611205541/http://genedose.com/, Jun. 11, 2017, 8 pages.

Coriell Life Sciences, DNA-Driven Diagnostics To Guide Clinical Decision-Making webpage, https://www.coriell.com/genetic-interpretation-reporting/, Sep. 11, 2019, 9 pages.

Coriell Life Services, GeneDose Youtube Video, https://youtube.com/watch?v=tku6_9tADuw, Sep. 11, 2019.

* cited by examiner

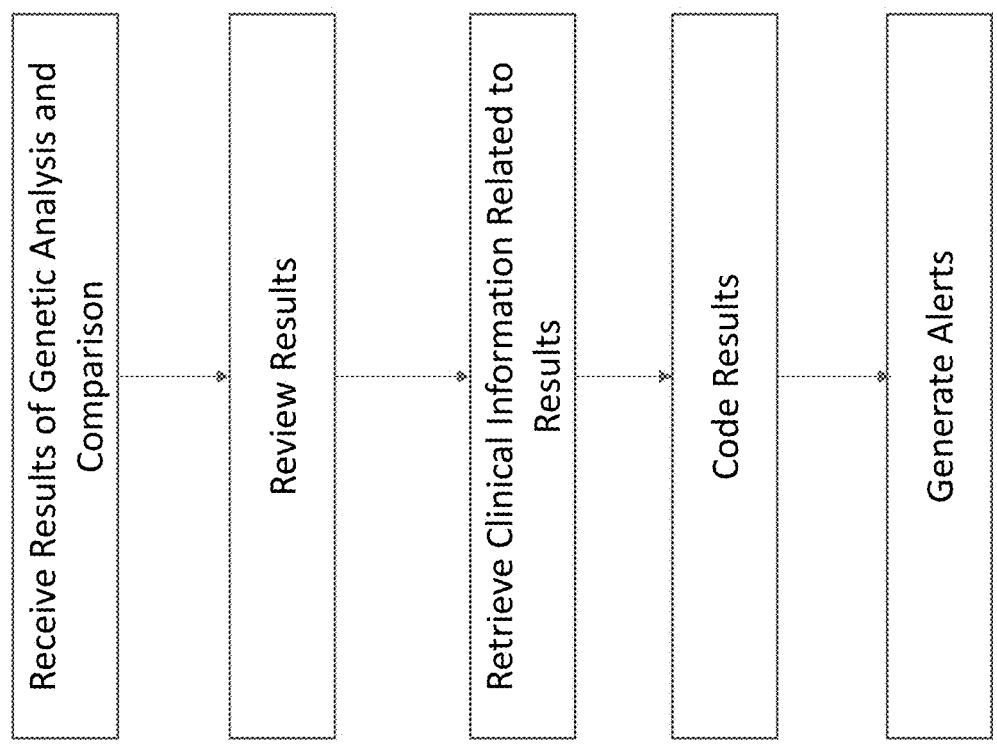

SYSTEM AND METHOD FOR GENETIC BASED EFFICACY TESTING

CROSS-REFERENCE TO RELATED APPLICATION

This application is a continuation-in-part of U.S. application Ser. No. 16/441,597 filed Jun. 14, 2019, which claims the benefit of U.S. Provisional Application Ser. No. 62/685,479 filed Jun. 15, 2018 and U.S. Provisional Application Ser. No. 62/773,424 filed Nov. 30, 2018, the disclosures of all of which are hereby incorporated by reference as if fully restated herein.

TECHNICAL FIELD

Exemplary embodiments relate generally to a system and method for genetic based efficacy testing.

BACKGROUND AND SUMMARY OF THE INVENTION

A person visiting a doctor may present with one or more symptoms. Based on the symptoms presented, test results, or underlying conditions or diseases diagnosed, the person may be prescribed one or more medications or other treatment options by the healthcare provider as part of a treatment program. These prescribed treatments may be selected based on the historical effectiveness of such treatment options against the symptoms presented by the person and/or the underlying disease(s) or condition(s) diagnosed by the healthcare provider. Traditionally, the prescription of treatment options is, at least initially, based on historical effectiveness. Individual prescriptions may be altered through a trial and error process following the initial prescription. For example, alternative medications, dosages, or other treatments (e.g., surgery, herbal remedies, other therapies) may be prescribed where the prescription of a particular treatment option causes a side effect or allergic reaction in a patient and/or simply fails to achieve the desired outcome. Over prescription or dosing of treatments, particularly of medications, may cause side effects or other undesirable consequences. Under prescription or dosing of treatments, particularly of medications, may bring about ineffective results, side effects, or other undesirable consequences.

A person's genetic makeup often affects how the person responds to certain medical treatments, such as the administration of medications. For example, a person's genetic makeup may cause some medications or dosages to be wholly or partially ineffective. As a further example, a person's genetic makeup may make surgery more or less desirable. Prescription of treatments to a person who has a genetic makeup that makes the treatment wholly ineffective may waste resources and unnecessarily expose the person to the risk of side effects. Similarly, prescription of treatments to a person who has a genetic makeup that makes the treatment partially ineffective may result in less that desirable therapeutic effects, require a larger dosage, or the like to be effective. In some cases, alternative medications, dosages, or other treatment options are available for use with the same, or similar, therapeutic effects.

For example, without limitation, a blood thinner may be known to reduce the risk of embolisms and may be prescribed to a person following stent placement. However, the patient's individual genetic makeup or physiology may alter the effectiveness of the prescribed blood thinner. For example, without limitation, the blood thinner may have a reduced effectiveness in persons carrying specific genetic markers. It would be desirable to substitute alternative medications or adjust the dosage of prescribed medications for persons having a genetic makeup which reduces the effectiveness of the prescribed medication. As a further example, again without limitation, the prescribed blood thinner may be wholly ineffective in persons carrying specific genetic markers. It would be desirable to substitute alternative medications, or find alternative treatment options, for persons having a genetic makeup which renders the prescribed medication ineffective. Therefore, what is needed is a system and method for determining the effectiveness of medications using genetics.

A persons' genetic makeup may determine the efficacy of other treatments beyond just medications. For example, without limitation, a persons' genomic makeup may be analyzed to determine the efficacy of various cancer treatment options. Such options may include various medications, such as chemotherapy, but may also include surgery, radiation, active surveillance, and the like.

Current systems, such as electronic medical record systems (EMR), are often unable to accept genomic information in a meaningful way and/or lack a dedicated space for such genetic information. For example, EMRs often do not have a designated page, portal, display, or the like for genomic testing results to be displayed. Therefore, what is needed is a system and method for integrating genetic efficacy information with existing systems.

Being a cutting-edge field, genomics testing is often not part of a healthcare provider's routine care plan. A healthcare provider may not even be aware that certain genomic testing is available that can determine the efficacy of various treatment options, such as medications. Therefore, what is needed is a system and method for determining eligibility for genetic efficacy testing.

These disclosures provide a system and method for determining the effectiveness of treatment options, such as medications, using genetic data. A user's visit information may be reviewed to identify applicable tests. For example, such tests may indicate the presence or non-presence of genetic markers which may indicate a genetic makeup for a patient that may have a bearing on the effectiveness of one or more treatments prescribed, or likely to be prescribed, to the user.

The disclosed systems and methods may be applied to any number of genomic efficacy tests. For example, without limitation, genomic testing may be ordered to determine the patient's likelihood of developing certain cancers and/or the efficacy of various treatment options for different types of cancer.

The disclosed systems and methods may also streamline the ordering and eligibility process. The system may determine whether identified tests fits certain billing parameters. For example, the system may be configured to determine whether the identified tests are covered by the user's insurance. If the test for one or more markers does not fit the billing parameters, then the next genetic marker(s) may be considered. If the test does fit the billing parameters then the option to order testing may be presented to the healthcare provider. If selected, the appropriate marker(s) may be added to a testing device and the genetic testing may be performed. In exemplary embodiments, diagnostic and treatment codes may be entered by the healthcare provider into their system. A determination may be made as to whether certain genetic efficacy testing meets various insurance eligibility criteria, such as but not limited to, medically necessary criteria. If so, the respective genomic tests may be automatically added to an order list. In this way, all available testing for which the patient is eligible may be automatically added to an ordering list, thereby increasing the availability of potentially relevant information to the healthcare provider.

To perform the testing, genetic material may be removed from the user. A testing device may be created to test for the specific genetic marker(s) ordered. The genetic material may be sequenced using the testing device and the presence or non-presence of the tested genetic markers may be determined. The results may be analyzed and ineffective treatment options, such as but not limited to medications, may be identified. In exemplary embodiments, for each treatment prescribed or likely to be prescribed, the presence or non-presence of one or more genetic markers may be analyzed and compared against the treatments known to be effective or ineffective in the presence of the given marker. Effective treatments and/or dosages may be identified. Alternatively, or additionally, ineffective treatments and/or dosages may be identified. For those treatments and/or dosages determined to be ineffective, alternative medications, dosages, and/or treatment options may be suggested.

Integration into existing EMR and other healthcare provider systems may be performed by designating ineffective medications or other treatment options as an allergy in the user's file. This may provide a pathway for integration with existing EMRs and other healthcare provider systems and advantageously, in exemplary embodiments, results in an alert being generated upon selection of a medication or other treatment options designated by the testing results to be ineffective. In this way, the disclosed systems and methods may be integrated within the framework of existing systems to prevent the costs and complexities of redesigning the existing systems.

Regardless, the testing results may be returned to the healthcare provider's system. For example, treatment of a particular disease may normally first begin with medication. However, if the person has a genetic makeup which would make such medication ineffective, a surgical option may instead be suggested.

The results may be returned to the healthcare provider in the form of an interface for display on an electronic display. The results may be displayed in a fashion which provides the clinical consequences of prescribing the treatment. The interface may further provide indications of particular conditions and generate alerts when particular conditions are met. For example, without limitation, executable software instructions may be provided which configure the electronic display to display an interface comprising an explanation of the results, alerts, abnormal ranges, ineffective treatments, potential interactions as understood in view of the analyzed genetic information, and other clinical information. This information may be transmitted with the results in a single file.

In exemplary embodiments, these results and alerts may be integrated into the healthcare providers' EMR by way of a single file. In exemplary embodiments, the results of the ordered tests, including but not limited to the ineffective treatment options, may be transmitted to a healthcare information exchange ("HIE"). The HIE may subsequently distribute the results to a number of linked healthcare provided systems and/or make such data available for access. This information may be further transmitted to any number of healthcare provider facilities, such as but not limited to hospitals, by way of one or more HIEs. For example, information may be transmitted to all healthcare providers treating the user. The results may also be stored for use by, and selective transmitted to, future healthcare providers. In this way, the disclosed systems and methods may integrate with existing healthcare provider systems, such as EMRs and HIEs to facilitate the ordering of such genomic efficacy tests and integrate the results into the framework of existing systems. Furthermore, integration with a number of healthcare provider systems may be accomplished by integration with one or more HIEs.

Further features and advantages of the devices and systems disclosed herein, as well as the structure and operation of various aspects of the present disclosure, are described in detail below with reference to the accompanying figures.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 8 is a simplified block diagram illustrating exemplary logic for analyzing genetic efficacy test results and generating alerts.

DETAILED DESCRIPTION OF EXEMPLARY EMBODIMENT(S)

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Figure 1B:
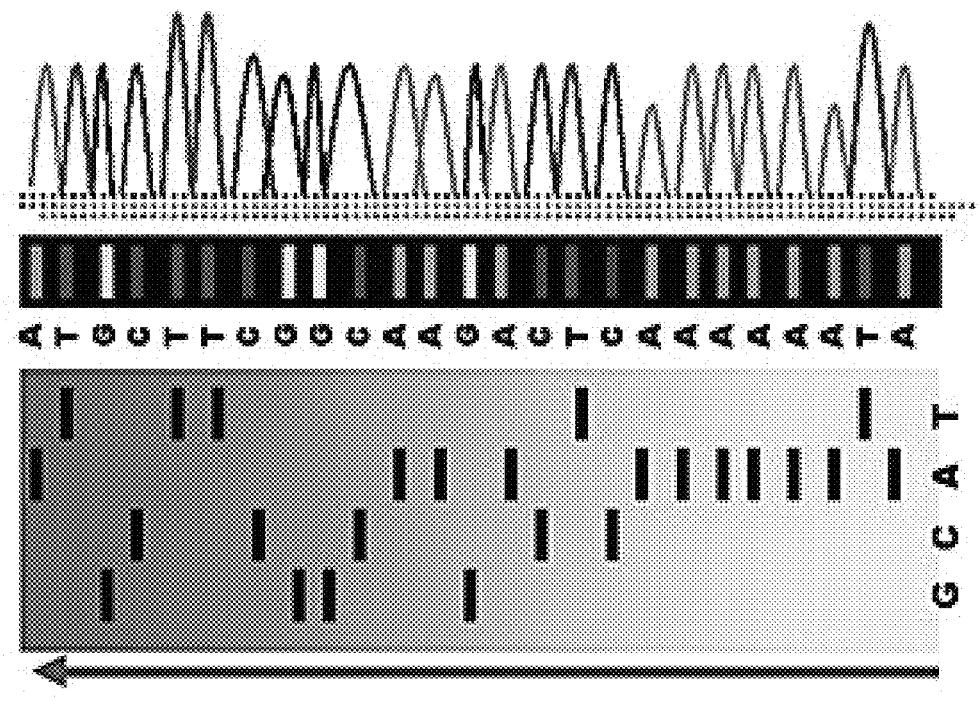
FIG. 1B is a simplified illustration of a DNA sequencing test result.
Figure 1A:
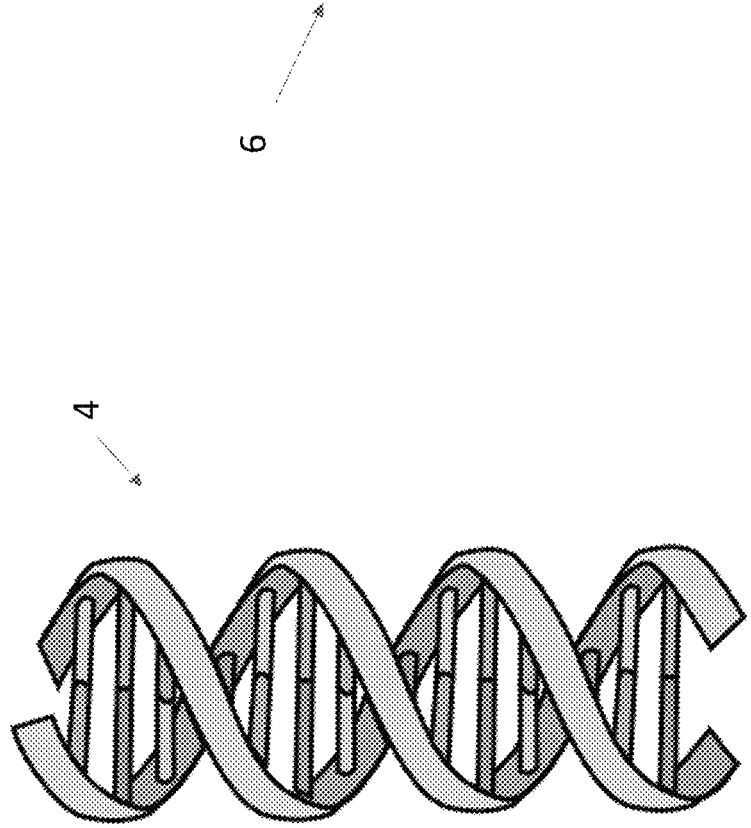
FIG. 1A is a simplified illustration of a DNA helix.

FIG. 1A is a simplified illustration of a DNA helix 4. DNA, or deoxyribonucleic acid, is a double-helix shaped chain of nucleotides that carry the genetic instructions used in the growth, development, functioning, and reproduction of all known living organisms. There are four major types of nucleobases in any nucleotide of a DNA sequence, which are generally coded as A, T, C, and G for adenine, thymine, cytosine, and guanine, respectively. Each individual human is believed to have a unique DNA structure that defines the persons' genetic makeup.

FIG. 1B is a simplified illustration of a DNA sequencing test result 6. Upon sequencing of the DNA 4, the presence or non-presence of particular nucleobases (A, T, C, or G) may be detected. The presence and non-presence or order of such nucleobases can be used to determine the presence or non-presence of certain genetic markers. The genetic markers may indicate the existence or non-existence of certain genetic traits for the person.

Figure 2:
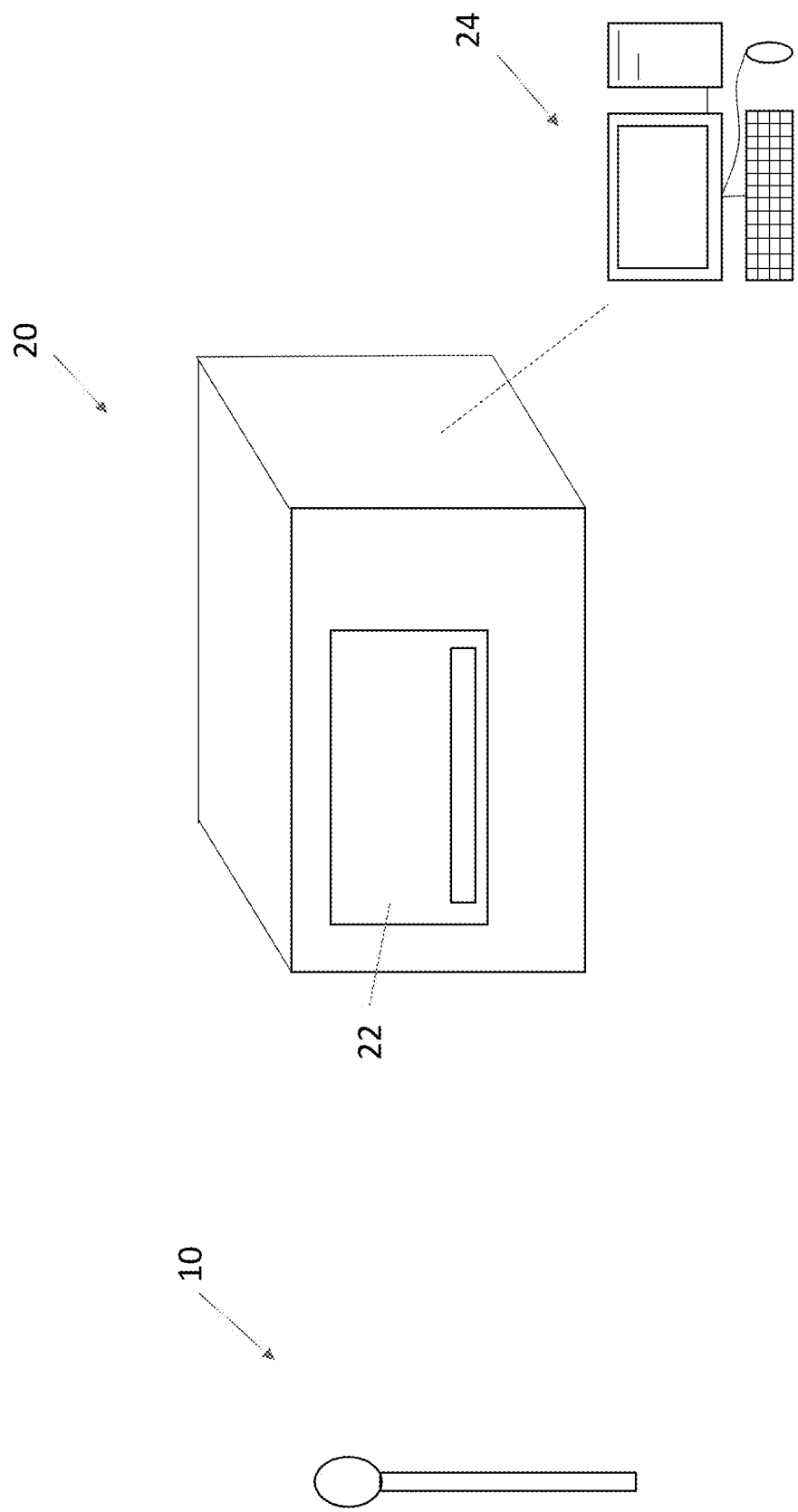
FIG. 2 is a simplified perspective view of an exemplary genetic material gathering device and an exemplary sequencing device.

FIG. 2 is a simplified perspective view of an exemplary genetic material gathering device 10 and an exemplary genetic sequencing device 20. The genetic material gathering device 10 may be a swab, syringe, vial, strip, or the like. For example, without limitation, the genetic material gathering device 10 may be a swab configured to be used on the inside of the user's cheek to gather saliva and/or skin cells. In other examples, without limitation, the genetic material gathering device 10 may be a syringe configured to gather blood, a vial configured to store blood, hair, skin samples, or the like, some combination thereof, or the like. Any type of genetic material gathering device 10 for gathering any type of genetic material is contemplated.

The genetic sequencing device 20 may be any kind of device configured to sequence genetic material. In exemplary embodiments, the genetic sequencing device 20 may comprise a loading area 22 and a control panel 24. The loading area 22 may be configured to accept one or more testing devices 30. The control panel 24 may be integrally formed with the genetic sequencing device 20 or may be a separate electronic device in communication with the genetic sequencing device 20. The control panel 24 may be configured to accept user input comprising instructions for carrying out various genetic tests on the testing device 30. The control panel 24 may be configured to display the results of such testing. Such instructions may, alternatively or additionally, be accepted from a remote device, which may be the control panel 24 or another device. Testing results may be transmitted to one or more remote devices and/or systems as further described herein.

Figure 3:
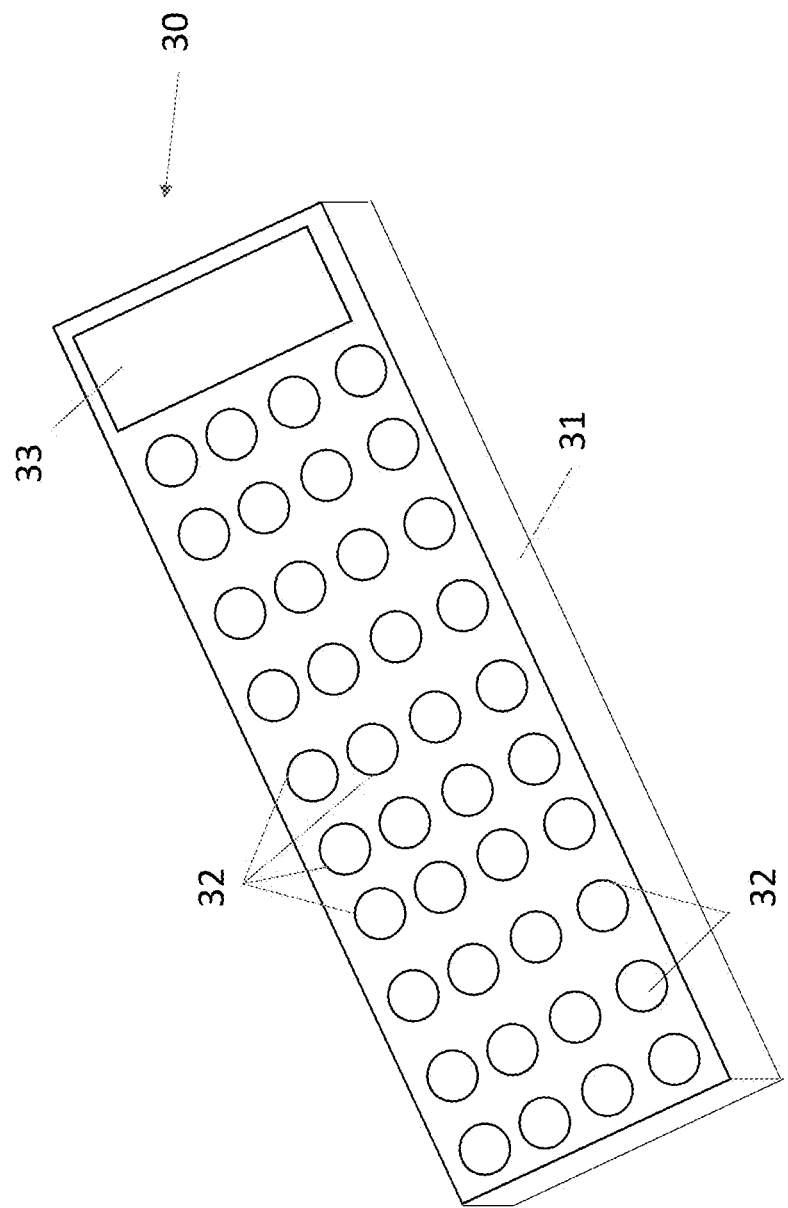
FIG. 3 is a simplified perspective view of an exemplary genetic testing device for use with the sequencing device of FIG. 2.

FIG. 3 is a simplified perspective view of an exemplary genetic testing device 30 for use with the sequencing device 20. In exemplary embodiments, the testing device 30 may be a chip 31 comprised of a number of wells 32, though any type of testing device 30 is contemplated. Each of said wells 32 may be configured to test for a particular genetic marker. The testing device 30 may be configured to accommodate any number of wells 32. In exemplary embodiments, certain wells 32 may be added or removed from the testing device 30 in order to test for the presence or non-presence of various genetic markers. For example, without limitation, wells 32 may be added to the chip 31 to test for particular genetic traits and wells 32 may be removed from the chip 31 if a particular genetic trait is not being tested for. In still other exemplary embodiments, the wells 32 being used may be placed in an unblocked position such that genetic material may enter the well 32. Similarly, the wells 32 not being used may be placed in a blocked position such that genetic material may not enter the wells 32. Modifications to the testing device 30 may be performed manually or automatically based on the instructions for testing received. For example, without limitation, the testing device 30 may be constructed or modified by one or more robots. The testing device 30 may further comprise one or more areas 33 to affix labels, markers, or the like.

Figure 4A:
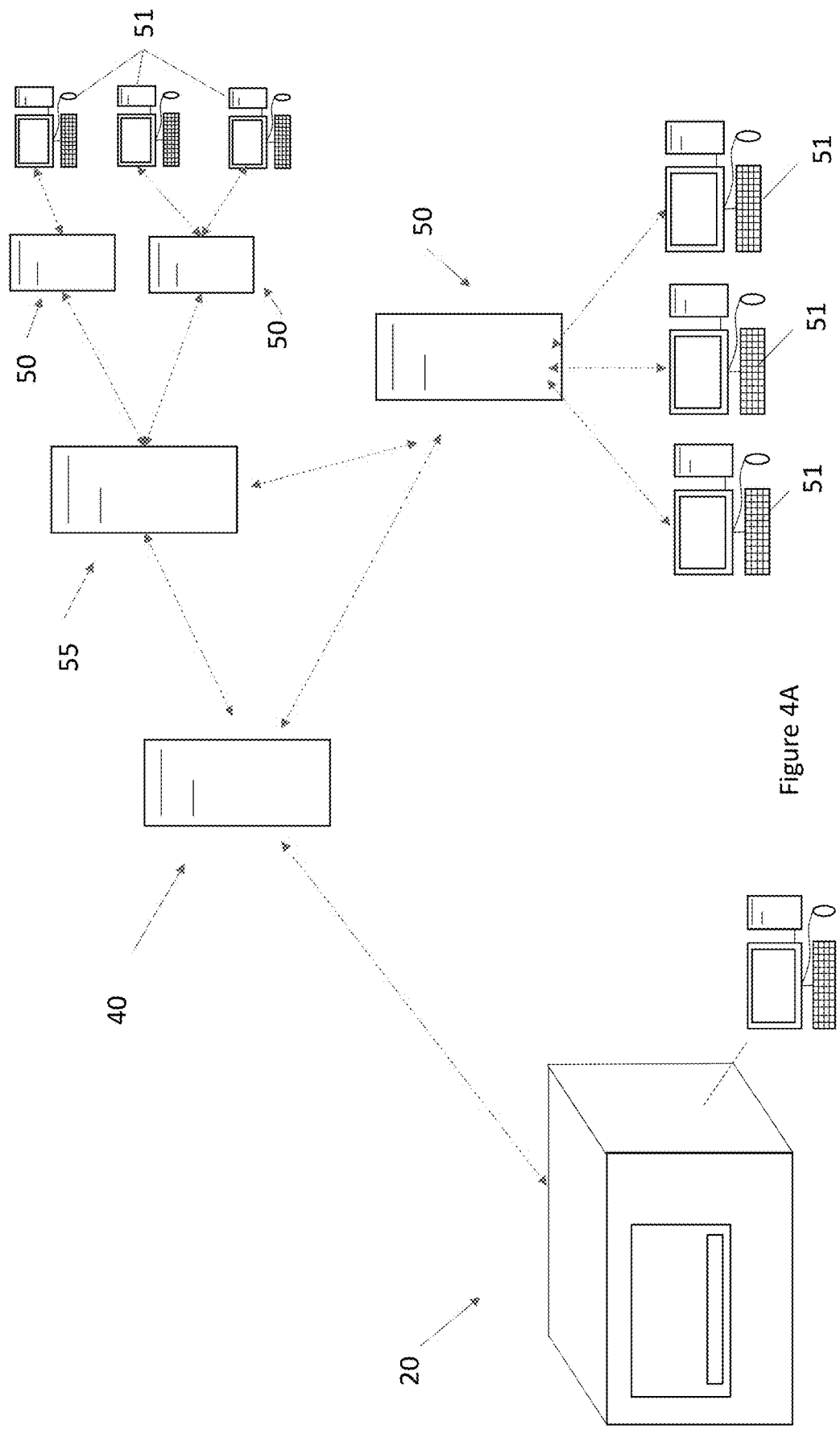
FIG. 4A is a simplified plan view of an exemplary system for providing genetic efficacy testing results, including the sequencing device of FIG. 2.

FIG. 4A is a simplified plan view of an exemplary system for providing genetic efficacy testing results. The genetic sequencing device 20 may be in electronic communication with a laboratory system 40. The laboratory system 40 may receive testing instructions which are communicated to one or more genetic sequencing devices 20. The laboratory system 40 may also be configured to receive the results of any performed tests from the one or more genetic sequencing devices 20. More than one laboratory system 40 may be provided, each of which may be in communication with one or more genetic sequencing devices 20. In exemplary embodiments, the laboratory system 40 may be a laboratory facing system. The laboratory system 40 may be in electronic communication with one or more healthcare provider systems 50. Each of the healthcare provider systems 50 may comprise patient information, a list of ordered tests, and test results, among other data. The healthcare provider systems 50 may communicate instructions for genetic efficacy tests to be performed to the laboratory system 40. The results of such ordered genetic efficacy tests may be transmitted from the laboratory system 40 to one or more of the healthcare provider systems 50. In exemplary embodiments, the healthcare provider systems 50 may be healthcare provider facing system such as, but not limited to, an electronic medical record ("EMR") system or the like. Although some embodiments are discussed with respect to a certain number of genetic sequencing devices 20, laboratory systems 40, and healthcare provider systems 50, any number of such components are contemplated.

The sequencing device 20, the laboratory system 40, and the healthcare provider system 50 may be located in the same facility, or may be remote from one another. The electronic communication may be by way of a wired or a wireless connection. The electronic communication may further be made by way of one or more network interface devices and one or more communication networks located at each of the sequencing device 20, the laboratory system 40, and the healthcare provider system 50. The communications networks utilized may include, but are not limited to, the internet, intranet, cellular network, or the like. In exemplary embodiments, communications between the genetic sequencing device 20, the laboratory system 40, and/or the healthcare provider system 50 may be made secured and encrypted. Alternatively, or additionally, such communications may be made in a standardized format such as, but not limited to, a HL7 format. In exemplary embodiments, the genetic efficacy test results may be pulled from the laboratory system 40 such as, but not limited, to by the use of scanning and archiving software. The testing results may be automatically integrated into the healthcare provider system 50. Such integration may be performed by way of a flat file, though any method of integration is contemplated. For example, without limitation, the testing results may be automatically integrated into the EMR utilized by the healthcare provider, preferably as further described herein.

Alternatively, or in addition, the test results may be made available to the healthcare provider by way of an internet-based portal accessed through the healthcare provider system 50 or any number of personal electronic devices 51 in electronic communication with, or constituting, the healthcare provider system 50. In particular, a hyperlink to the portal may be provided to the healthcare provider system 50 such that it is stored as a quick link access, though such is not required. As yet another example, without limitation, the testing results may be provided to the healthcare provider by way of email to the healthcare provider system 50. In other embodiments, the testing results may be made available to the healthcare provider by way of an application installed on the various personal electronic devices 51.

The test results stored on the laboratory system 40 may be secured such that a particular healthcare provider can only access the results for users associated with the particular healthcare provider. For example, without limitation, permission may be set such that login credentials associated with a given healthcare provider may be permit access to test results for particular users associated with that healthcare provider. The laboratory system 40 may be configured to periodically download testing results from the genetic sequencing device 20. Similarly, the laboratory system 40 may be configured to periodically download testing results to the healthcare providers system 50. Alternatively, or in addition, certain results may be downloaded on demand. Access to the testing data, including but not limited to testing results, may be protected by way of security protocols, such as, but not limited to, authentication, biometric scanning, single sign-on, barcode scanning protocols, some combination thereof, or the like.

Each of the sequencing devices 20, the laboratory systems 40, and the healthcare provider systems 50 may comprise one or more electronic components. Such electronic components may include, but are not limited to, processors, electronic storage devices, user input devices, displays, and the like. Each of the sequencing devices 20, the laboratory systems 40, and the healthcare provider systems 50 may comprise software instructions configured to perform the steps and functions described herein.

Figure 4B:
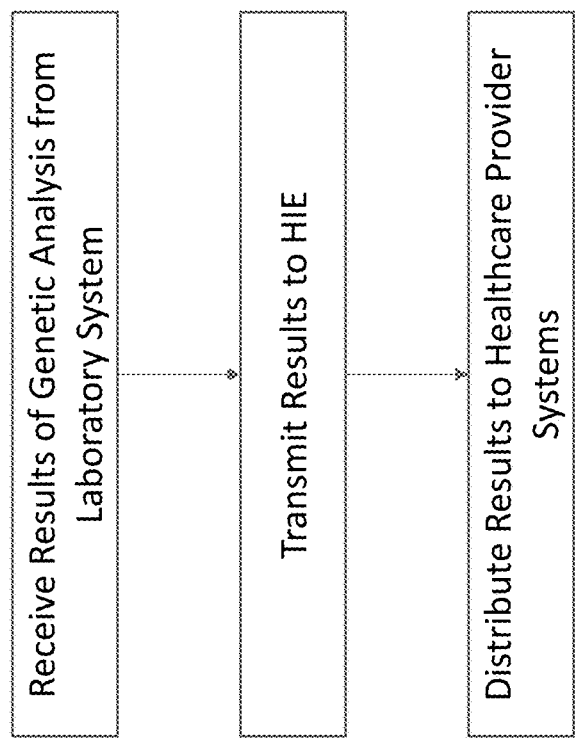
FIG. 4B is a flow chart with exemplary logic for distributing the test results.

FIG. 4B is a flow chart with exemplary logic for distributing the genetic efficacy test results. In exemplary embodiments, test results may be received from the laboratory system 40 at a health care information exchange ("HIE") 55. The HIE 55 may be in electronic communication with a number of healthcare provider systems 50. Each of the healthcare provider systems 50 may be in electronic communication with one or more personal electronic devices 51. The HIE 55 may be configured to automatically distribute the test results to each healthcare provider system 50 associated with a healthcare provider known to be treating the patient. In other exemplary embodiments, the HIE 55 may make the testing results available for integration into any of the linked healthcare provider systems 50.

In exemplary embodiments, the necessary integration of the laboratory system 40 and/or genetic efficacy test results may be performed only with respect to a single HIE 55 to permit integration with a number of linked healthcare provider systems 50. This also may permit information for specific data, such as but not limited to unusual cases, to be shared across healthcare providers who may be geographically remote from one another and/or associated with different practices such that the most relevant information may be made available to healthcare decision makers. For example, without limitation, the efficacy data for a patient seen with a relatively rare genetic makeup in Connecticut may be sent to a doctor in Oregon who has a different patient with a similar genetic makeup.

Figure 5A:
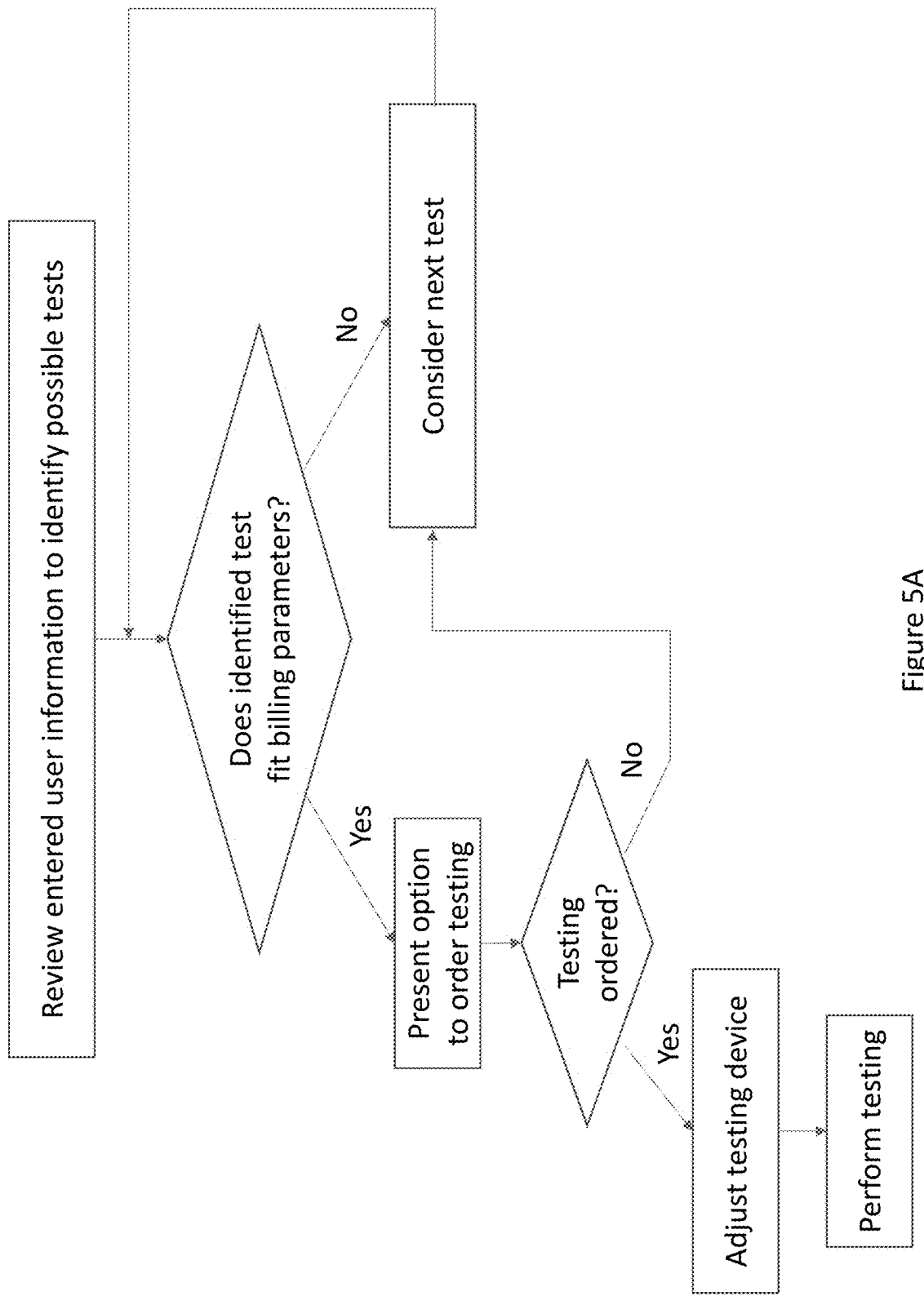
FIG. 5A is a flow chart illustrating exemplary logic for identifying, ordering, and performing tests.

FIG. 5A is a flow chart illustrating exemplary logic for identifying, ordering, and performing genetic efficacy tests. A user may visit one or more healthcare providers and present with a variety of symptoms. As the healthcare provider evaluates the user, including by taking a medical history, evaluating symptoms, and performing tests, the healthcare provider may enter information about the user into the healthcare providers' system 50. Already existing information about the user may already be present on the healthcare providers' system 50, though such is not required. Such information already existing or entered by the healthcare provider might include, for example but without limitation, demographic information, insurance information, medical history, known allergies, family history, some combination thereof, and the like. In exemplary embodiments, the healthcare provider system 50 is an EMR. The entered information by the healthcare provider at a given visit may include, for example but without limitation, treatment actions taken or prescribed, symptoms presented, diagnosed diseases or conditions, tests ordered, testing results, some combination thereof, and the like. In exemplary embodiments, at least the treatment actions taken or prescribed and the diseases or conditions diagnosed may be entered and/or converted into codes, such as but not limited to, ICD codes, though any type, protocol, or format of coding is contemplated.

In exemplary embodiments, certain information about the patient may be retrieved by the laboratory system 40 from the healthcare provider system 50 such as, but not limited, to by the use of scanning and archiving software. The laboratory system 40 may review the entered information and identify conditions diagnosed, or likely to be diagnosed, treatments prescribed, or likely to be prescribed, to the patient. The treatments likely to be prescribed, such as but not limited to medications, may be determined by comparing the entered information with standard treatment procedures. Such standard treatment procedures may be stored at the laboratory system 40, or at one or more separate databases, and may be sourced from public and private data sources. For example, without limitation, if a stent placement is ordered for the patient, the laboratory system 40 may determine that post-operative blood thinners are likely to be prescribed. The conditions likely to be diagnosed may be determined by comparing the entered information, such as symptoms and test results, with diseases associated with such information. Such disease information may be stored on the laboratory system 40, or one or more separate database, and may be sourced from public and private data sources. For example, without limitation, if chest pain is reported, a likely condition of heart disease may be determined.

The laboratory system 40 may identify one or more genetic markers that may have a bearing on the effectiveness of prescribed, or likely to be prescribed, treatments. The laboratory system 40 may determine whether testing for the identified genetic markers fits one or more billing parameters. For example, without limitation, the laboratory system 40 may determine whether such testing would be considered medically necessary under Medicare regulations and/or guidelines. An exemplary listing of medically necessary codes is provided in tables 1-2 below. The provided tables are merely exemplary and are not intended to be limiting.

TABLE 1

Cardiovascular Diagnostic Codes

| Code | Description |
|---|---|
| 120.0 | Unstable angina |
| 120.1 | Angina pectoris with documented spasm |
| 120.8 | Other forms of angina pectoris |
| 120.9 | Angina pectoris, unspecified |
| 121.09 | ST elevation (STEMI) myocardial infarction involving other coronary artery of anterior wall |

TABLE 1-continued

Cardiovascular Diagnostic Codes

| Code | Description |
| --- | --- |
| 121.11 | ST elevation (STEMI) myocardial infarction involving right coronary artery |
| 121.19 | ST elevation (STEMI) myocardial infarction involving other coronary artery |
| 121.29 | ST elevation (STEMI) myocardial infarction involving other sites |
| 121.3 | ST elevation (STEMI) myocardial infarction of unspecified site |
| 121.4 | Non-ST elevation (NSTEMI) myocardial infarction |
| 124.0 | Acute coronary thrombosis not resulting in myocardial infarction |
| 124.1 | Dressler's syndrome |
| 124.8 | Other forms of acute ischemic heart disease |
| 124.9 | Acute ischemic heart disease, unspecified |
| 125.110 | Atherosclerotic heart disease of native coronary artery with unstable angina pectoris |
| 125.700 | Atherosclerosis of coronary artery bypass graft(s), unspecified, with unstable angina pectoris |
| 125.710 | Atherosclerosis of autologous vein coronary artery bypass graft(s) with unstable angina |
| 125.720 | Atherosclerosis of autologous artery coronary artery bypass graft(s) with unstable angina pectoris |
| 125.730 | Atherosclerosis of nonautologous biological coronary artery bypass graft(s) with unstable angina pectoris |
| 125.750 | Atherosclerosis of native coronary artery of transplanted heart with unstable angina |
| 125.760 | Atherosclerosis of bypass graft of coronary artery of transplanted heart with unstable angina |
| 125.790 | Atherosclerosis of other coronary artery bypass graft(s) with unstable angina pectoris |

TABLE 2

Psychiatric and Pain Management Diagnostic Codes

| Code | Description |
| --- | --- |
| F31.30 | Bipolar disorder, current episode depressed, mild or moderate severity, unspecified |
| F31.31 | Bipolar disorder, current episode depressed, mild |
| F31.32 | Bipolar disorder, current episode depressed, moderate |
| F31.4 | Bipolar disorder, current episode depressed, severe, without psychotic features |
| F31.5 | Bipolar disorder, current episode depressed, severe, with psychotic features |
| F31.60 | Bipolar disorder, current episode mixed, unspecified |
| F31.61 | Bipolar disorder, current episode mixed, mild |
| F31.62 | Bipolar disorder, current episode mixed, moderate |
| F31.63 | Bipolar disorder, current episode mixed, severe, without psychotic features |
| F31.64 | Bipolar disorder, current episode mixed, severe, with psychotic features |
| F31.75 | Bipolar disorder, in partial remission, most recent episode depressed |
| F31.76 | Bipolar disorder, in full remission, most recent episode depressed |
| F31.77 | Bipolar disorder, in partial remission, most recent episode mixed |
| F31.78 | Bipolar disorder, in full remission, most recent episode mixed |
| F31.9 | Bipolar disorder, unspecified |
| F32.9 | Major depressive disorder, single episode, unspecified |
| F33.0 | Major depressive disorder, recurrent, mild |
| F33.1 | Major depressive disorder, recurrent, moderate |
| F33.2 | Major depressive disorder, recurrent severe without psychotic features |
| F33.3 | Major depressive disorder, recurrent, severe with psychotic symptoms |
| F33.40 | Major depressive disorder, recurrent, in remission, unspecified |
| F33.41 | Major depressive disorder, recurrent, in partial remission |
| F33.42 | Major depressive disorder, recurrent, in full remission |
| F33.9 | Major depressive disorder, recurrent, unspecified |
| G10 | Huntington's disease |

In exemplary embodiments, if any of the diagnostic codes provided by the healthcare provider system 50 fit the provided billing parameters, then the genetic testing may automatically be included in the plan of treatment for that patient.

Alternatively, or additionally, the laboratory system 40 may be configured to gather and review insurance information for coverage eligibility for particular types of testing. The laboratory system 40 may be configured to determine whether such testing would be wholly or partially covered by the user's insurance. This may be performed by reviewing the billing codes against those codes covered by the user's insurance. This may alternatively or additionally be performed by interfacing with the user's insurance provider. Regardless, in such embodiments, the billing parameters may comprise the testing known or likely to be approved. These billing parameters may be predetermined and preprogramed and may be selected based on the user's insurance coverage.

Alternatively, or in addition, the laboratory system 40 may be configured to generate one or more forms for gathering and authorizing payment information for desired testing. For example, without limitation, the laboratory system 40, or a separate payment system, may be configured to store and authorize credit card transactions to pay for the ordered testing. This option may be provided to, for example without limitation, users who do not have insurance or elect not to bill insurance for such testing. This option may also be provided to cover any co-payment, patient responsible portions, some combination thereof, or the like. In such cases, the billing parameters may be any testing elected by the user.

Regardless, if the test fits the billing parameters, then an option to order testing may be presented to the healthcare provider at the healthcare provider system 50. If not, then the test for the next genetic marker may be considered. Alternatively, or additionally, if the test fits the billing parameters, it may be automatically added to a list of ordered tests.

If the healthcare provider orders the test, or the test is automatically added, the appropriate wells 32 may be added to, or removed from, the testing device 30 to test for the specified genetic markers. Alternatively, or in addition, the appropriate wells 32 may be blocked or unblocked on the testing device 30 to test for the specified genetic markers. Once all identified tests are considered, instructions for assembly of the testing device 30 may be transmitted and the testing may be performed.

In exemplary embodiments, user information may be gathered, or presented, using one or more secured means. For example, without limitation, information may be gathered and entered into the personal electronic devices 51 running a secured browser application. The personal electronic devices 51 may comprise remote shunt down capabilities and a variety of security protocols, such as but not limited to, authentication, biometric scanning, single sign-on, barcode scanning protocols, some combination thereof, or the like may be utilized.

Other information gathered from the user may include scanned copies of insurance card and photo ID. Forms such as digital consent forms, educational information, questionnaires, and medical necessity forms may be digitally filled out, stored, and/or transmitted. The laboratory system 40 and/or the healthcare provider system 50 may be configured to generate a QR code, barcode, label, or other identifier for attachment to the genetic material gathering device 10, the genetic testing device, paperwork, some combination thereof, or the like. Scanning of the QR code, barcode, label, or another identifier may automatically retrieve the associated user information.

Figure 5B:
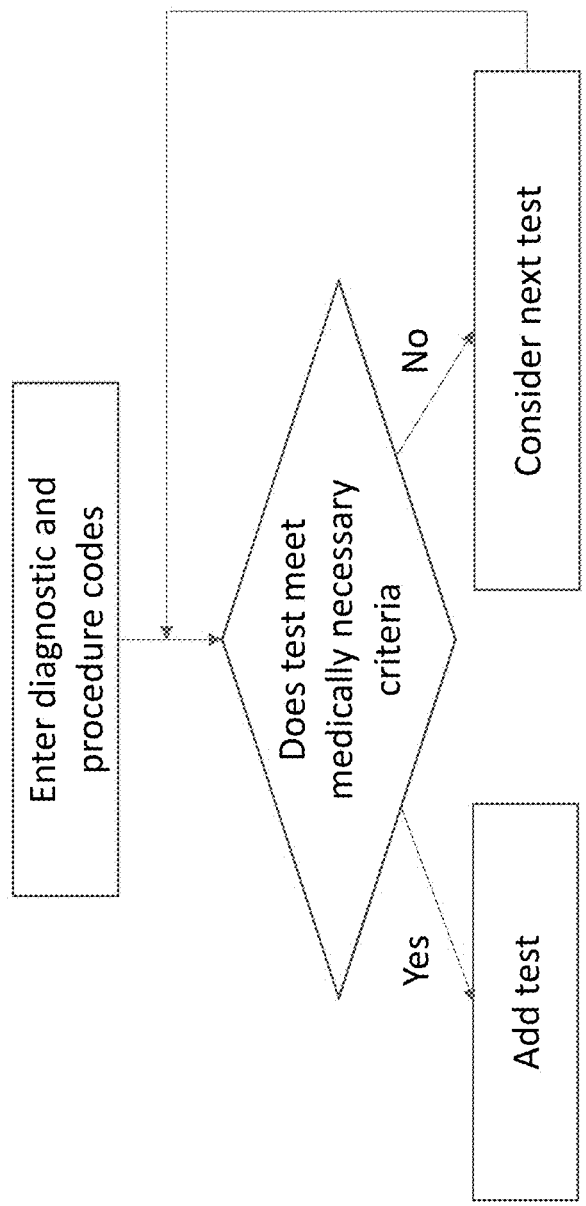
FIG. 5B is a flow chart illustrating other exemplary logic for identifying and ordering tests.

FIG. 5B is a flow chart illustrating other exemplary logic for identifying and ordering tests. Diagnostic and/or procedure codes may be entered by the healthcare provider. Preferably, such diagnostic and/or procedures codes are entered at the respective personal electronic device 51 for the respective healthcare provider system 50. The diagnostic and/or procedure codes may conform to International Classification of Diseases ("ICD"), though any type, standard, protocol, etc. of coding is contemplated. If the diagnostic and/or procedure codes meet medically necessary criteria for a given genetic efficacy test, for example without limitation, then the test may be automatically added to a list of ordered tests to be transmitted to the laboratory system 40. If the diagnostic and/or procedure codes fail to meet medically necessary criteria, for example without limitation, then the next test may be considered until all possible tests are exhausted.

Once all tests are considered, the list of order tests may be transmitted to the laboratory system 40. The diagnostic and/or procedure codes may be utilized to determine which genetic efficacy tests are relevant. In other exemplary embodiments, a list of particular genetic test may be considered for each patient. The medically necessary criteria may be under Medicare and/or Medicaid guidelines, though any protocol, standard, or the like is contemplated. Other criteria are contemplated in addition to, or as an alternative to, the medically necessary criteria.

In this way, eligible test results may be automatically added to an order. Being a cutting-edge field, genomic efficacy testing is sometimes unknown or under considered by healthcare providers. The disclosed systems and methods not only permit the determination of insurance eligibility for such testing, but may automatically add such eligible tests to help ensure that a patient receives the highest quality of care and maximizes the information available to healthcare providers.

Figure 6A:
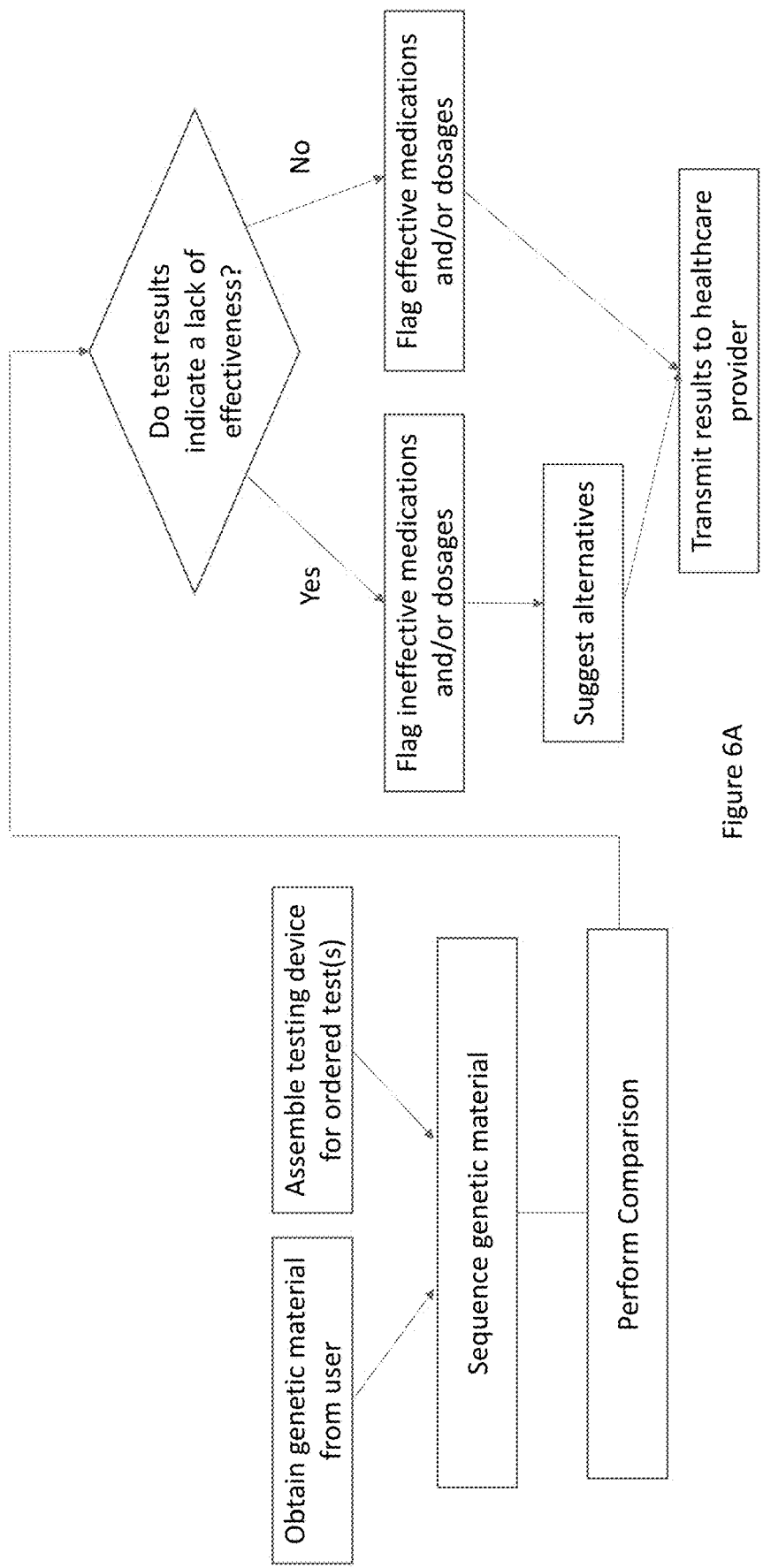
FIG. 6A is a flow chart illustrating exemplary logic for performing genetic efficacy testing and analyzing results.

FIG. 6A is a flow chart illustrating exemplary logic for performing genetic efficacy testing and analyzing results. Genetic material from the user may be gathered by way of the genetic material gathering device 10. A genetic testing device 30 comprising wells 32 for the ordered testing may be assembled. Such assembly may be performed manually or automatically. Such assembly may be performed concurrently, before, or after obtaining the genetic material. The genetic material may then be sequenced using the genetic sequencing device 20.

The testing may determine the presence or non-presence of the genetic markers for which the testing is performed. The results of such testing may be transmitted to the laboratory system 40. The results may be compared against information stored in the laboratory system 40, or elsewhere, regarding the effectiveness of given treatment options, such as but not limited to medications, in persons having or not having particular genetic markers. In particular, the results may be compared for each of the treatments prescribed to the user, or likely to be prescribed to the user. Similarly, the results may be compared against information stored in the laboratory system 40, or elsewhere, regarding the need for particular dosages or treatments in persons having or not having particular genetic markers. In particular, the results may be compared for each of the treatments and/or dosages prescribed to the user, or likely to be prescribed to the user. Such information may be gathered from one or more public or private sources such as, but not limited to, the human genome project. In exemplary embodiments, the laboratory system 40, the healthcare provider system 50, and/or another system may be configured to prompt the healthcare provider to perform a follow-up telephone call regarding the test results a period of time after electronically transmitting the results to the patient.

The laboratory system 40 may flag ineffective treatments and/or dosages. Likewise, the laboratory system 40 may flag effective treatments and/or dosages. In exemplary embodiments, the results may be color coded. For example, without limitation, red color coding may indicate an ineffective treatment and/or dosage. A yellow color coding may indicate the need to adjust the treatment and/or dosage or monitor use of the therapy. A green color coding may indicate that the treatment and/or dosage is acceptable. Other colors and types of coding are contemplated.

The results of the testing may be transmitted to the healthcare provider system 50. The laboratory system 40 may be configured to automatically suggest alternative medications, or dosages, or treatment options for those treatments flagged to be ineffective or requiring adjustments. Furthermore, the healthcare provider system 50 may be updated to reflect the ineffectiveness of the treatments and/or dosages. For example, without limitation, ineffective treatments may be flagged or otherwise coded as an allergy in the user's file. More specifically, ineffective treatments may be identified in the message to the healthcare provider. For example, without limitation, this information may be added to the HL7 electronic results, such as but not limited to the PathX HL6 electronic communication, that are received with the test results and embedded into any .pdf type files generated from the HL7 file.

Alternatively, or in addition, additional parties may be notified of treatments and/or dosages determined to be ineffective. Such parties may include, but are not limited to, pharmacists, project managers, healthcare practice administrators, insurance providers, users, other healthcare providers, other approved persons, and the like. The results of the testing may be transmitted to each parties' respective system 50.

One or more healthcare information exchanges ("HIEs") may be utilized to provide information between various systems 50 and individuals. For example, without limitation, the results of the testing may automatically be shared with the healthcare provider system 50 for each healthcare provider treating the user. Each healthcare provider treating the user may automatically be granted access to the results of the testing, such as by way of the respective healthcare provider's personal electronic device 51. In exemplary embodiments, the HIE may provide two-way communication such that information may be transmitted to and from the laboratory system 40.

Figure 6B:
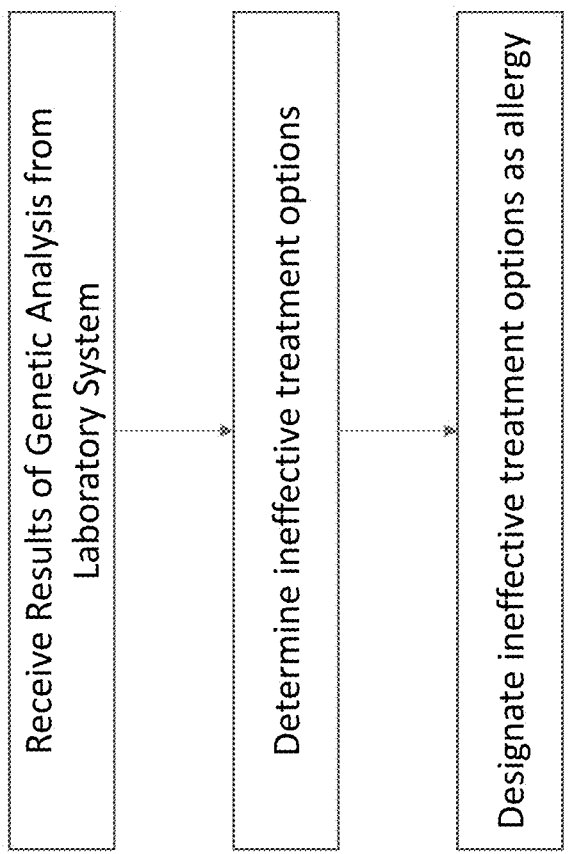
FIG. 6B is a flow chart illustrating exemplary logic for integrating genetic efficacy test results within existing systems.

FIG. 6B is a flow chart illustrating exemplary logic for integrating genetic efficacy test results within existing healthcare provider systems 50. Existing healthcare providers system 50, such as but not limited to EMRs, may not have a dedicated space for the integration of genomic testing results. Redesigning existing systems to provide such a dedicated space would be time consuming and expensive. As such, in exemplary embodiments, after receiving the genetic efficacy testing results and determining which treatment options are ineffective and/or have a reduced efficacy, such treatment options may be designated as an allergy in the user's file. Many, if not all, existing healthcare provider systems 50 have a designated space for the notation of allergies. As such, this provides a pathway for integration of genomic efficacy testing results into the patient's electronic file. Helpfully, in many cases, the healthcare provider system 50 is configured to raise an alert or otherwise provide some kind of notification upon prescription of such treatments flagged as an allergy. In this way, for example without limitation, ineffective medications and/or dosages may be alerted to the healthcare provider when ordering at the healthcare provider system 50.

Figure 7:
FIG. 7 is an exemplary healthcare provider interface.

FIG. 7 is an exemplary healthcare provider interface 60. The healthcare provider interface 60 may be displayed on one or more personal electronic devices 51 in electronic communication with the healthcare provider system 50. The personal electronic devices 51 may be computers, smartphones, tablets, or the like. The interface 60 may provide results for one or more patients. The interface 60 may alternatively, or in addition, provide the results for multiple medications for a one or more patients. In exemplary embodiments, the results may be presented with the clinical consequences of prescribing each of the therapies. For example, without limitation, the interface 60 may inform the healthcare provider of whether the prescribed therapy is likely to be effective, partially effective, wholly ineffective, or the like. The healthcare provider interface 60 may be updated for each individual healthcare provider user 62. The healthcare provider's recently accessed files may be identified 64. A quick links section 66 may include a link to the portal for test ordering and results. A schedule 68 may include one or more indicators 70 which patient(s) have possible warnings associated with their test results. For example, without limitation, the results may be color coded. Such warnings may be provided as a result of coding the ineffective treatment options as an allergy in the user's file.

In other exemplary embodiments, indicators 70 may be presented in the form of alerts. Such alerts may include pop-ups, warning signals, electronic messages, or the like. Such indicators 70 may be generated upon the receipt of results which indicate that the healthcare provider has prescribed a treatment, such as but not limited to a drug, to a patient known to be a non-responder to such treatments, the presence of abnormal result or range, the prescription of a treatment known to cause an allergic effect in the patient, or the prescription of a treatment which may potentially cause an interaction with a drug previously prescribed to the patient, or with a disease the patient is diagnosed with as understood in view of the analyzed genetic information. Other clinical information may be transmitted and displayed on the interface 60 such as, without limitation, an explanation of the results.

FIG. 8 is a simplified block diagram illustrating exemplary logic for analyzing genetic efficacy test results and generating alerts. Once the results of the genetic analysis are received, they may be reviewed. The review may include a comparison against information known about the patient, for example, by analyzing the patient's medical records as stored at one or more of the healthcare provider systems 50. For example, without limitation, the results may be reviewed to determine if the healthcare provider has prescribed, or is likely to prescribe, a treatment, such as but not limited to a drug, to a patient known to be a non-responder to such treatments, if the results include an abnormal result or range, if the healthcare provider has prescribed a treatment known to cause an allergic effect in the patient, and/or if the healthcare provider has prescribed a treatment which may potentially cause an interaction in view of the analyzed genetic information. The clinical information required to support this analysis may be retrieved from one or more databases, such as but not limited to, the healthcare provider system 50 or a database comprising various known medical information such as known drug interactions based on genetic makeup, normal results or ranges for various medical tests, and the like. The results of this review may be used to code the results displayed at the interface 60 or generate alerts as appropriate.

The comparison, analysis, and the like described herein may be performed at the laboratory system 40 or at the healthcare provider system 50. It is contemplated that any type of clinical information may be transmitted for display at the interface 60. The genetic information and test results may be stored at the laboratory system 40, the healthcare provider system 50, and/or another system to also be used against future prescribed treatments. In this way, the testing results may stay with the patient such that they can be referred to in the future as a person's genetic makeup generally remains unchanged throughout their life.

The clinical consequence of prescription, in exemplary embodiments, may be added to the electronic results and embedded into a single file for transmission to the healthcare provider system 50. This may remove the need for use of multiple file types between the laboratory system 40, the healthcare provider system 50, and the electronic displays or individual systems 51. This may alternatively, or in addition, remove the need for multiple file types to be transmitted to one of the aforementioned systems. For example, one file with the results and another file with any alerts or other clinical information, though such an embodiment is contemplated. In exemplary embodiments, the results and all other related clinical information may be transmitted in a single standardized file, such an HL7 type file, though any file type is contemplated. This may permit the report to be integrated into any EMR system. In other exemplary embodiments, such clinical consequences may be transmitted by designating the particular treatment options likely to be ineffective or undereffective as an allergy. In exemplary embodiments, the genetic information and/or test results may be temporarily stored at the laboratory system 40 and/or another electronic storage device such that the data may be reformatted or otherwise modified as required to integrate with the HIE 55 and/or the various healthcare provider systems 50.

The coding and alerts described herein may be individualized based on the preferences of each user or entity. For example, when communicating results to a first healthcare provider system 50, alerts may be generated only when certain predetermined conditions are met. Likewise, when communicating results to a second healthcare provider system 50 alerts may be generated only when other predetermined conditions are met which may be the same or different from (with some overlap, complete overlap, or no overlap) with the predetermined conditions used to generate alerts for communications to the first healthcare provider system 50. Similarly, preferences may be altered for each personal electronic device 51.

In exemplary embodiments, the results may be transmitted along with educational information regarding the genetic testing results, a space for progress notes, and order information. In exemplary embodiments, the laboratory system 40, the healthcare provider system 50, or another system, may automatically schedule a follow up telephone encounter for approximately 1 week after the results are transmitted or the order is placed for testing.

Any embodiment of the present invention may include any of the optional or preferred features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

Certain operations described herein may be performed by one or more electronic devices. Each electronic device may comprise one or more processors, electronic storage devices, executable software instructions, and the like configured to perform the operations described herein. The electronic devices may be general purpose computers of specialized computing device. The electronic devices may be personal computers, smartphone, tablets, databases, servers, or the like. The electronic connections described herein may be accomplished by wired or wireless means.

What is claimed is:

1. A system for providing genetic efficacy testing results to a number of users, the system comprising:
   a number of user systems, each comprising medical records information, an electronic display, diagnostic codes indicating various diseases or conditions diagnosed by healthcare providers for patients, and treatment codes indicating various treatments prescribed by the healthcare providers to the patients;
   a number of personal electronic device, each in electronic communication with at least one of said user systems;
   a database comprising data regarding medications known to have reduced or no efficacy in persons having particular genetic markers;
   a healthcare information exchange system ("HIE") in electronic communication with each of the user systems;
   a genetic sequencing machine; and
   a laboratory system in electronic communication with the healthcare information exchange system, the database, and the genetic sequencing machine, wherein the laboratory system comprises a processor and an electronic storage device comprising software instructions, which when executed, configure the processor to:
   receive the diagnostic codes and the treatment codes for a particular patient;
   determine if tests for each of a number of genetic markers qualify as medically necessary based upon the diagnostic codes and the treatment codes received for the particular patient;
   perform testing for each of the genetic markers qualifying as medically necessary;
   receive testing results from the genetic sequencing machine indicating the presence or non-presence of each of the genetic markers tested;
   query the database to determine whether any treatments associated with the treatment codes received are known to have reduced or no efficacy in persons having same ones of the genetic markers as those found to be present in the testing results; and
   generate an alert comprising the treatments having reduced or no efficacy;
   wherein said healthcare information exchange is configured to transmit the alert to at least the user systems associated with the healthcare provider ordering the tests and authorized to view the alert;
   wherein the personal electronic devices associated with the user systems receiving the alerts are each configured to store and display said alert in an allergy portion of the user system.

2. The system of claim 1 wherein:
said database comprises a list of alternative treatment options; and
said laboratory system comprises additional software instructions stored at the electronic storage device, which when executed, configure the processor to determine alternative treatment options from the list of alternative treatment options stored at the database for each of the treatments having reduced or no efficacy.

3. The system of claim 2 wherein:
the treatments comprise medications; and
the alternative treatment options comprise other medications.

4. The system of claim 1 wherein:
the user systems authorized to view the alerts comprise user systems associated with a payor for the particular patient.

* * * * *